United States Patent
Weitz et al.

(10) Patent No.: US 7,690,791 B2
(45) Date of Patent: Apr. 6, 2010

(54) METHOD FOR PERFORMING MICRO-PERIMETRY AND VISUAL ACUITY TESTING

(75) Inventors: Rishard Weitz, Downsview (CA); Duncan McLean, Kingston (CA); John Rogers, Canterbury (GB); Justin Pedro, Waterloo (CA)

(73) Assignee: OTI Ophthalmic Technologies Inc. (CA)

( * ) Notice: Subject to any disclaimer, the term of this patent is extended or adjusted under 35 U.S.C. 154(b) by 0 days.

(21) Appl. No.: 12/265,127

(22) Filed: Nov. 5, 2008

(65) Prior Publication Data
US 2009/0141240 A1 Jun. 4, 2009

Related U.S. Application Data

(60) Provisional application No. 60/985,465, filed on Nov. 5, 2007.

(51) Int. Cl.
*A61B 3/00* (2006.01)
*A61B 3/02* (2006.01)

(52) U.S. Cl. .................. 351/246; 351/237; 351/239
(58) Field of Classification Search .......... 351/205–246
See application file for complete search history.

(56) References Cited

U.S. PATENT DOCUMENTS

| 5,757,546 A * | 5/1998 | Lipton et al. ............. 359/464 |
| 6,089,715 A * | 7/2000 | Hoover et al. ............ 351/221 |
| 2002/0013573 A1* | 1/2002 | Telfair et al. ................ 606/5 |
| 2007/0115481 A1* | 5/2007 | Toth et al. ................ 356/511 |

* cited by examiner

*Primary Examiner*—Mohammed Hasan
(74) *Attorney, Agent, or Firm*—Lawrence E. Laubscher, Jr.

(57) ABSTRACT

A visual acuity examination is performed on a patient by bringing a confocal imaging apparatus up to a patient's eye. Stimuli at various points in the patient's field of view are generated while the patient fixates on a point. The patient's responses to the stimuli are recorded with the movement of the eye with is tracked with the aid of the confocal imaging apparatus. The position of said stimuli on the retina is corrected to take into account any movement of the eye between stimuli.

6 Claims, 2 Drawing Sheets

METHOD FOR PERFORMING MICRO-PERIMETRY AND VISUAL ACUITY TESTING

CROSS REFERENCE TO RELATED APPLICATION

This application claims the benefit of prior U.S. provisional application Ser. No. 60/985,465, filed Nov. 5, 2007, the contents of which are herein incorporated by reference.

FIELD OF THE INVENTION

This invention relates to field of opthalmological examination, and in particular to a method for performing micro-perimetry and visual acuity examinations of a patient.

BACKGROUND OF THE INVENTION

Visual field tests designed to map a person's visual field and document the level of peripheral vision are a mainstay in opthalmology. Such tests are used to assess disease and treatment progressions. Typically, the test consists of having the patient respond every time a flash of light is perceived while the patient looks straight ahead, fixating onto a point. Visual acuity is normally tested using charts projected onto a wall where the patient is asked to read letters. Perimetry examination are used to test point locations on the retina and are commonly performed using a Humphrey™ field analyzer.

A major drawback of both of these systems is the lack of fundus tracking. For instance, if someone has 20/200 vision in his or her macular, but 20/40 vision in his or her periphery, a standard visual field test will not discern the difference, or tell the doctor what part of the fundus the patient is using to fixate. The fundus is the interior part of the eye opposite the lens.

A standard perimetry examination provides no tracking. Projecting stimuli to patients with poor fixation gives meaningless results if the patient moves his eye between stimuli.

SUMMARY OF THE INVENTION

According to the present invention there is provided a method of performing a visual acuity examination on a patient comprising bringing a confocal imaging apparatus up to a patient's eye; displaying stimuli at various points in the patient's field of view while the patient fixates on a point; recording the patient's responses to said stimuli; tracking movement of the eye with said confocal imaging apparatus; and correcting the position of the stimuli on the patient's retina to take into account any movement of the eye between successive stimuli.

Thus, in accordance with an embodiment of the invention, SLO imaging from a combined Scanning Laser Opthalmoscope and Optical Coherence Tomography (SLO/OCT) system is used to image the eye while stimuli are displayed to the patient. Software automatically tracks the motion of the eye during the examination. This gives the doctor valuable information, such as what parts of the eye the patient is using to fixate, helps ensure the accuracy of the test, and provides the doctor with an excellent fundus image for use in diagnosis.

As soon as the acuity or perimetry exam is complete, the patient can be scanned using the OCT portion of the system so the doctor can see structural information from the patient's eye by performing B-Scans, C-Scans, or obtaining a 3D tomography. The functional (perimetry and acuity) information can then be overlaid on the structural information so the doctor can see which structures in the eye correlate to visual loss.

Having functional and structural capabilities built into a single machine means less examination time is required for a patient, less training is required for the operator, and more accurate information can be delivered to the doctor.

BRIEF DESCRIPTION OF THE DRAWINGS

The invention will now be described in more detail, by way of example only, with reference to the accompanying drawings, in which.

DETAILED DESCRIPTION OF THE INVENTION

A commercially available combined SLO/OCT system is described, for example, in U.S. Pat. No. 6,769,769, the contents of which are herein incorporated by reference. Such an SLO/OCT system is capable of making OCT images of the eye or retina as well as SLO or confocal microscopic images.

Figure 4:
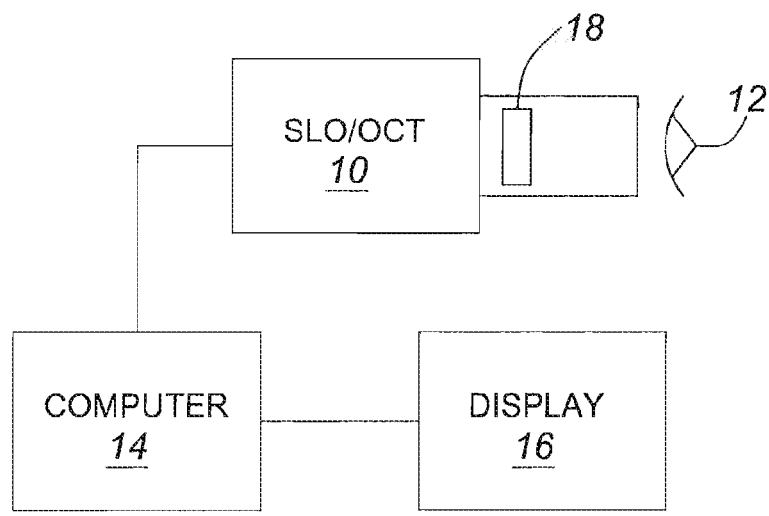
FIG. 4 is a block diagram of an apparatus for performing a visual acuity examination in accordance with one embodiment of the invention.

In accordance with an embodiment of the invention, a visual acuity examination is performed while the patient's eye motion is tracked using high resolution SLO scans generated by the SLO-OCT system. As shown in FIG. 4, the SLO-OCT system 10 is brought up to the patient's eye 12, and a series of SLO images of the retina obtained by scanning. The confocal images are created by computer 14 from the SLO scans and displayed on display screen 16.

The SLO-OCT system 10 is able to track movement of the retina by comparing successive images. The tracking can be performed automatically in software in the computer 14 using any of a number of known algorithms suited for this purpose, such as a combination of edge detection and Hausdroff's algorithm for image alignment. The actual algorithm used is not important as long as it is able to accurately track the eye motion.

The SLO-OCT system 10 includes a high resolution display 18, controlled by the computer 14, that the patient can see while being scanned. The high resolution display 18 is used to create a fixation target for the patient to fixate on. The patient is asked to fixate on the target while the examination is performed by generating the stimuli at various points in the patient's field of view and at various intensities. For example, if the patient is looking at a central point, a flash may be generated at a location described by polar coordinates $r_1, \theta_1$, and the patient asked to indicate whether he can observe this flash. The intensity of the flash can be changed to determine the patient's responsiveness at this point. The process can then be repeated at different points, $r_i, \theta_i$.

Figure 1:
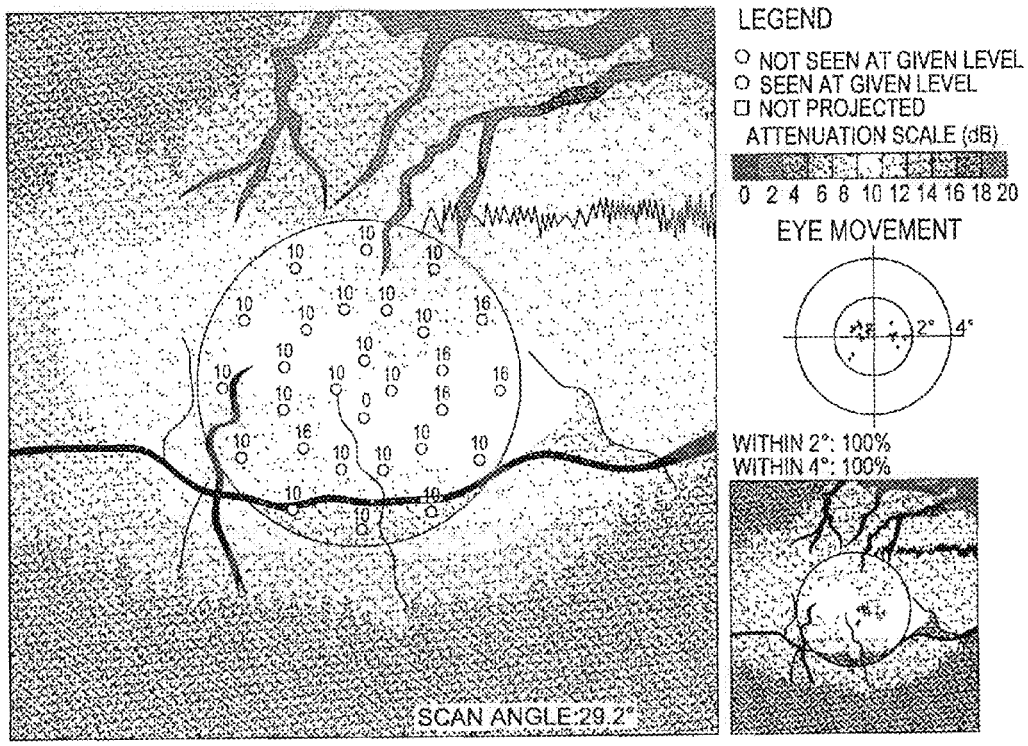
FIG. 1 is a picture of the retina showing the results of a perimetry exam.

The resulting tracking data obtained from the SLO-OCT system are then used with the display 18 to accurately place the perimetry stimuli on the same fundus location for each point tested taking into account any patient movement. Thus, based on the patient's responses, a map of the patient's acuity field, as shown in FIG. 1, can be created. By taking into account the eye motion detected by the SLO imaging apparatus between scans, the data points can be correlated to the correct positions on the patient's retina. For example, if the SLO imaging apparatus detects that the retina moved an amount δx between successive stimuli, the position of the later stimulus point on the retina can be adjusted to take this movement into account.

Figure 2:
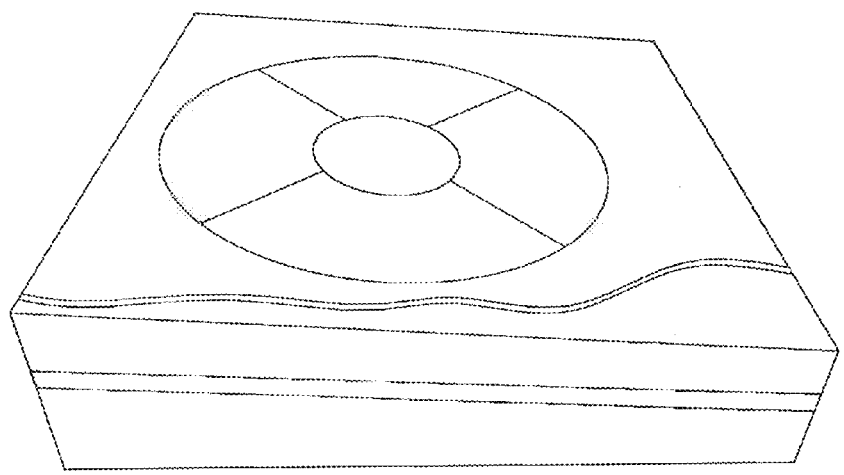
FIG. 2 is an OCT topographic image (False color indicates retinal thickness, black and white are OCT B-Scans)
Figure 3:
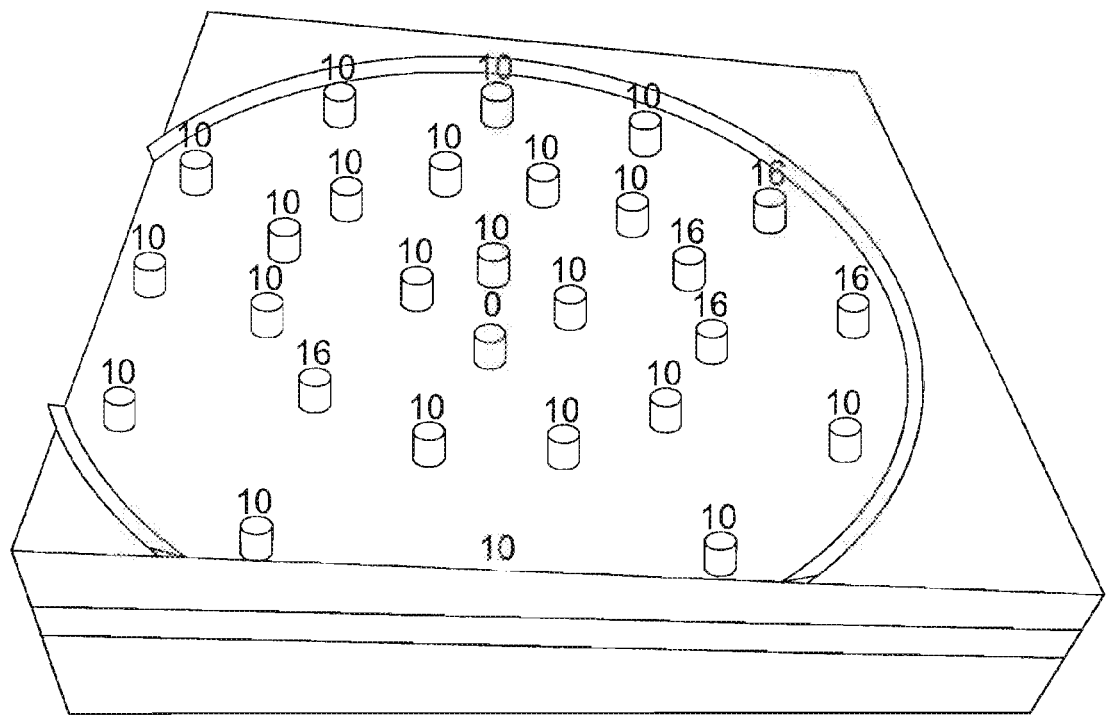
FIG. 3 shows the results of a perimetry examination overlaid on the topographic image.

In addition, a tomographic three dimensional image, shown in FIG. 2, can be obtained using the OCT portion of the apparatus, in which case the stimuli points can be marked on the 3D image as shown in FIG. 3.

The display can also be used to display a Snellen 'C' in one of four orientations (opening of the C up, down, left, or right). In this test, the patient uses a hand-held controller or joystick to report the direction of the opening. When the patient can no longer tell the direction of the opening, he has passed the limit of their visual acuity. Any number of other letters or symbols can be used for the same purpose. The tracking data obtained by the SLO apparatus can be recorded to show which part of the eye the patient was using to fixate on the fixation point.

The invention takes advantage of the functional and structural information that the SLO-OCT system can generate. It may desirably use automatic alignment of SLO images from function and structural imaging to overlay perimetry or acuity results on B-Scans, C-Scans or topographies in the computer 14.

Aspects of the invention thus include a method for integrating micro-perimetry exams into a combined imaging SLO-OCT system, and a method for integrating acuity exams into a combined imaging SLO-OCT system.

We claim:

1. A method of performing a visual acuity examination on a patient comprising the steps of:

bringing a confocal imaging apparatus up to a patient's eye having a retina;

presenting a display to the patient;

displaying stimuli at various points on the target on the display in the patient's field of view while the patient fixates on a point on the target;

recording the patient's responses to said stimuli;

creating a succession of images of the retina with said confocal imaging apparatus while displaying said stimuli;

comparing said successive images to track movement of the retina; and creating a map of the patient's acuity field from the responses to said stimuli taking into account any movement of the retina between successive stimuli determined by comparing said successive images.

2. A method as claimed in claim 1 wherein said map is overlaid on a confocal image of the retina obtained with said confocal imaging apparatus.

3. A method as claimed in claim 1, wherein said confocal imaging apparatus is a combined SLO/OCT apparatus, and said map is overlaid on a tomographical image of the retina obtained by using the OCT portion of the apparatus.

4. A method as claimed in claim 1, wherein said stimuli comprise light flashes, and the intensity of said light flashes is varied to determine the patient's response over different regions of the retina.

5. A method as claimed in claim 1, wherein a shape is displayed to the patient on said display, and the limit of visual acuity is determined by having the patient report the orientation of the shape.

6. A method as claimed in claim 5, wherein said shape is a C-shape.

* * * * *